United States Patent [19]

Napolitano

[11] Patent Number: 4,850,865
[45] Date of Patent: Jul. 25, 1989

[54] ORTHODONTIC METHOD AND APPARATUS

[76] Inventor: John R. Napolitano, 204 E. Hicks, Palatine, Ill. 60067

[21] Appl. No.: 44,587

[22] Filed: Apr. 30, 1987

[51] Int. Cl.$^4$ .............................................. F26B 13/00
[52] U.S. Cl. ......................................... 433/8; 433/20
[58] Field of Search ..................... 433/8, 9, 10, 13, 15, 433/17, 20, 23

[56] References Cited

U.S. PATENT DOCUMENTS

| | | | |
|---|---|---|---|
| 2,386,124 | 10/1945 | Laskin | 433/20 |
| 3,327,393 | 6/1967 | Brader | 433/13 |
| 3,486,231 | 12/1969 | Nelson | 433/13 |
| 3,772,787 | 11/1973 | Hanson | 433/14 |
| 3,797,115 | 3/1974 | Silverman et al. | 433/3 |
| 3,946,488 | 3/1976 | Miller et al. | 433/11 |
| 3,959,880 | 6/1976 | Andrews | 433/11 |
| 4,180,912 | 1/1980 | Kesling | 433/13 |
| 4,197,642 | 4/1980 | Wallshein | 433/11 |
| 4,260,375 | 4/1981 | Wallshein | 433/11 |
| 4,424,033 | 1/1984 | Wool | 433/20 |
| 4,565,526 | 1/1986 | Kawata et al. | 433/8 |

FOREIGN PATENT DOCUMENTS 573245 3/1976 Switzerland .......................... 433/20

OTHER PUBLICATIONS

Unitek Orthodontic Materials Catalog 118, pp. 73, 74, 1978 edition.

Primary Examiner—Noah P. Kamen
Attorney, Agent, or Firm—Welsh & Katz, Ltd.

[57] ABSTRACT

An improved orthodontic apparatus is provided having one or more brackets adapted for mounting on the surface of a tooth. The brackets have a wire receiving slot formed therein with non-parallel slot surfaces. A tapered wire having non-parallel oppositely disposed wire surfaces is also provided. When the wire is positioned in the wire receiving slot and placed under tension, a selected force vector is effected against the tooth. The wire surfaces and the wire receiving slot surfaces may be configured so as to selectively wedge the wire in the slot or provide slidability, as desired. A series of inserts may further be provided for selectively altering the force vectors effected against the tooth. A method and system for utilizing the aforesaid brackets and tapered wire are thereby provided.

13 Claims, 2 Drawing Sheets

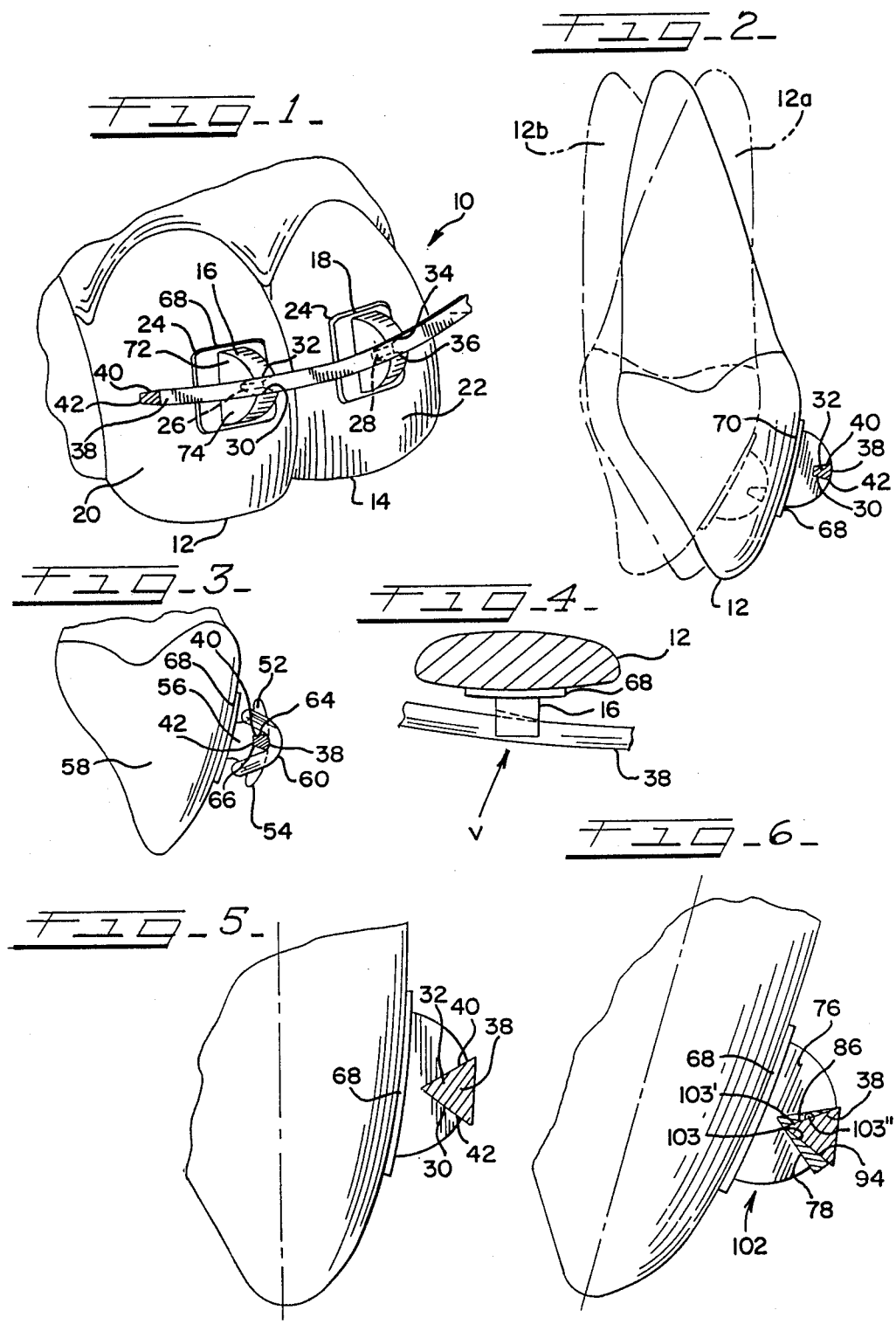

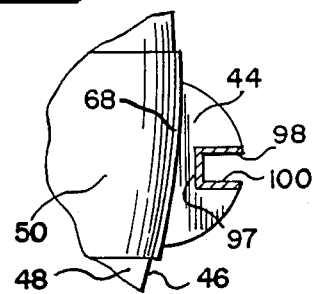
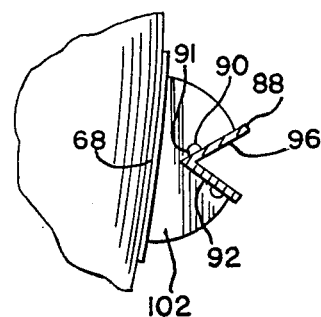
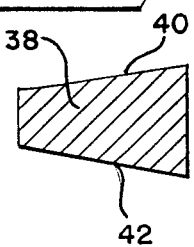
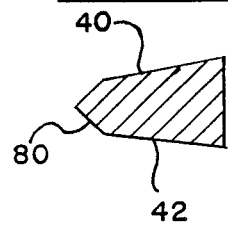
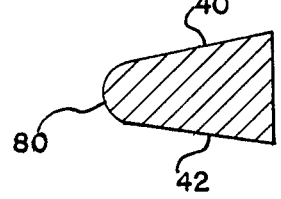
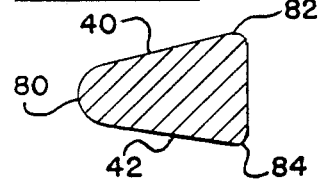
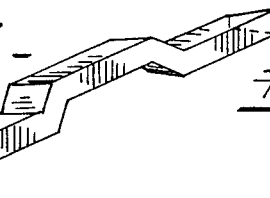
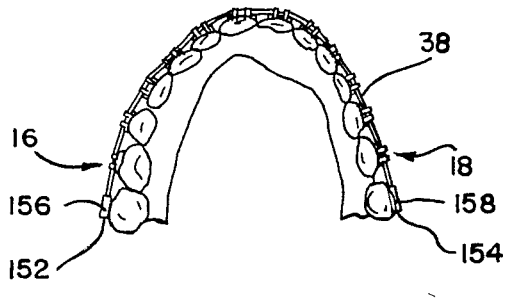
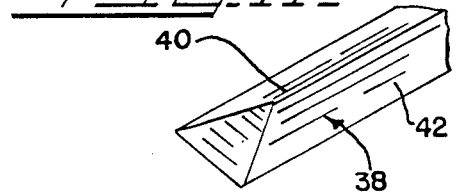

ORTHODONTIC METHOD AND APPARATUS

BACKGROUND OF THE INVENTION

The present invention relates generally to orthodontia and more particularly to an improved method and apparatus for orthodontic correction utilizing tapered arch wires and tapered wire receiving slots in the arch wire brackets.

As is well known to those versed in orthodontics, initial positioning and application of brackets and arch wires is a tedious and time consuming procedure and especially difficult when the patients are youngsters. While there have been a significant number of devices developed for positioning of brackets and arch wires, considerable problems remain. In addition, reducing the number of arch wires and the replacement of arch wire brackets, particularly in lingual braces, is highly desirable.

In the science of orthodontics there has been developed two techniques and the associated apparatus for straightening teeth. The "edgewise" technique was developed first and employs orthodontic brackets having a horizontal slot for receiving a single rectangular arch wire. The arch wire is retained by brackets attached to adjacent teeth and is bent to achieve "tipping" (rotation of the tooth about the buccal-lingual axis toward or from adjacent teeth) or "torquing" (rotation of the tooth about the mesial-distal axis toward or from the palate). The rectangular arch wire is usually relatively large in diameter and is painful to the patient since large rotational forces are generated.

The "light-wire" technique was developed in an attempt to avoid the painfully large rotational forces of the "edgewise" technique. A thin round wire is utilized to reduce the rotational forces while achieving results which are as effective as those obtained with large rectangular or round wires. In addition there is less friction between the bracket and the wire so that the teeth can move much more easily.

U.S. Pat. No. 3,327,393 Brader discloses an orthodontic arch wire edgewise bracket having a pair of coacting resilient arms which hold a conventional arch wire in the bracket. The resilient arms are spaced and rounded so as to provide an opening aligned with the entrance of the wire receiving chamber. The arch wire may be either rectangular or trapezoidal with the trapezoidal configuration augmenting the differences and the resistance of the lip surfaces to the insertion and removal of the arch wires, thereby making it easier to insert the arch wire and more difficult to remove it. The wire receiving socket is described in Brader as being shaped to cooperate with the arch wire; however, there is no teaching as to how they cooperate.

U.S. Pat. No. 3,964,165 Stahl, discloses a wire retaining bracket made of an elastomeric polymer. The bracket has a horizontal slot with a liner formed of a substantially rigid material such as metal. The bracket may be molded around the liner to form an integral unit. However, removal or replacement of the liner is not suggested.

At the present time, the most popular orthodontic technique is called the Begg technique after its inventor. It employs a rectangular bracket having a rectangular slot and a round wire. The round wire is used to exert force against the tooth by means of the bracket. The crown of the tooth goes backward and the tip of the root comes forward. Because the wire is round and the bracket is narrow, there is little friction and movement is rapid, but since only the root is moving forward, the net effect is not desirable.

One way of solving the problem of uncontrolled tipping is the use of rectangular wire. When a tooth is retracted on rectangular wire it moves back more or less in a bodily fashion with little or no tipping. However, movement of the tooth in a force vector other than directly horizontal or vertical is not easily accomplished with rectangular wire.

Accordingly, it is an object of the present invention to provide an improved apparatus for the orthodontic correction of teeth which utilizes a tapered arch wire and a tapered wire receiving slot so as to effect orthodontic correction in three planes of space simultaneously.

It is an additional object in one embodiment of the present invention to provide an apparatus for orthodontic correction which utilizes a plurality of bracket inserts for selectively increasing or reducing friction when changing the position of the arch wire and for altering the force vector applied to the tooth being corrected.

It is an additional object of the present invention to provide a system for orthodontic correction in which the arch wire, the brackets and the inserts are visually coded so that perfect duplicability of orthodontic correction may be effected.

Finally, it is an additional object of the present invention to provide a nathological method of orthodontia in which the entire patient is treated.

SUMMARY OF THE INVENTION

The present invention relates generally to orthodontic apparati and in a particular to a novel system of nathological orthodontic correction utilizing tapered arch wires, and arch wire brackets having tapered arch wire slots so as to provide slidability or friction to the arch wire as may be desired. The tapered arch wire and arch wire brackets are further adapted for directing a selected force vector against the tooth being corrected. The arch wire brackets may also be adapted for attachment to inserts which direct the force vector applied by the arch wire and/or reduce friction. A system of arch wire brackets and/or inserts utilizing a visual coding is further provided. Finally, in one embodiment, a self-ligating orthodontic method and apparatus is disclosed. The aforesaid components may be utilized individually or collectively so as to provide improved orthodontic methods.

In one embodiment of the invention, an orthodontic apparatus is provided which includes one or more brackets adapted for attachment to the surface of a tooth, each of the brackets including a wire receiving slot having oppositely disposed non-parallel slot surfaces. A tapered wire having non-parallel oppositely disposed wire surfaces is adapted for slidable positioning of the tapered wire into the wire receiving slot. As a result, the position of the wire may be adjusted while mounted in the brackets. The tapered arch wire may be triangular, rounded, trapezoidal or a combination of the above. The non-parallel wire surfaces are preferably disposed at substantially the same angle as the relative oppositely disposed non-parallel slot surfaces. The angle is selected so as to facilitate either slidable engagement or wedging of the tapered wire in the wire receiving slot, as required. The brackets may be attached to the tooth utilizing a band tightly circumscribing the tooth or an adhesive for direct attachment.

In one embodiment, the arch wire is self-ligating, i.e., does not require the assistance of external locking mechanisms to remain in the arch wire slot. This is accomplished by having the non-parallel oppositely disposed wire surfaces disposed at an angle of between 1 degree and 25 degrees and at substantially the same angle relative to each other as the oppositely disposed non-parallel slot surfaces. In addition the wire receiving slot is sized relative to the wire so as to facilitate selective wedging of the wire in the wire receiving slot and retention therein without the assistance of external locking mechanisms.

In a preferred embodiment, the brackets each comprise a base adapted for attachment to one of the teeth, and a pair of arms disposed substantially normally from the base with the wire receiving slot being disposed between the arms. Alternatively, a rounded crown can extend from the base with the wire receiving slot being disposed across the surface thereof.

In one embodiment of the invention, one or more insert members are inserted into the wire receiving slot. The insert members have an external configuration substantially identical to the wire receiving slot so as to be adapted for insertion into and attachment to the wire receiving slot. The insert member and the wire receiving slot preferably have their non-parallel surface at an angle of between 1 degree and 25 degrees so as to wedge therein. The insert members further have a wire receiving slot which may have a high slip surface adapted for facilitating slidability of the wire in the wire receiving slot or a surface adapted for wedging of the tapered wire, as required. Although in a preferred embodiment the external configuration of the insert slot may be tapered, in some embodiments the external configuration of the insert may be rectangular and the internal configuration of the wire receiving slot tapered. Alternatively, both the wire receiving slot and the insert slot may be rectangular with the insert being constructed of a high slip material such as Teflon.

An additional aspect of the invention is the use of the system described above for progressive orthodontic correction. A series of bracket members each including an insert slot is provided. A series of insert members is also provided, each having a wire receiving slot adapted for reception of an arch wire. The wire receiving slots are progressively tapered so that a selected force vector may be applied against the tooth being corrected. Further, the insert members are selectively insertable or removable in the insert slot so as to selectively alter the force vectors applied against the teeth. Thus, as the teeth are moved by orthodontic correction, the force applied against the tooth can be altered as required.

In order to facilitate use of the system, the brackets, insert members and arch wires may be visually coded to indicate the type of correction provided. The elements of the system can be coded by color or number. Similarly, the arch wires can be progressively thicker and/or stiffer and may be visually coded to indicate the stiffness provided, so that a selected force vector can be applied against the tooth being corrected. A series of tools are provided for inserting and removing the insert members.

In summary, a method and apparatus is provided for effecting highly precise orthodontic correction.

BRIEF DESCRIPTION OF THE DRAWINGS

FIG. 1 of the drawings is a front perspective view of an orthodontic apparatus having a plurality of brackets and a tapered arch wire.

FIG. 2 of the drawings is a side elevational view of one of the teeth of FIG. 1 showing in particular a side view of the bracket and arch wire, partially broken away.

FIG. 3 of the drawings is a side elevational view, partially broken away, of an alternative embodiment of the orthodontic apparatus of FIG. 1, showing in particular a bracket and tapered arch wire having a ligature fixedly attaching the arch wire to the bracket.

FIG. 4 of the drawings is a top sectional view, partially broken away, of the tooth and bracket of FIG. 1 showing in particular the wire receiving slot of the bracket being tapered on three surfaces in order to effect a selected force vector against the tooth.

FIG. 5 of the drawings is a side elevational view, partially broken away, of a tooth, bracket and tapered arch wire in which the arch wire and arch wire receiving slot are substantially triangular.

FIG. 6 of the drawings is a side elevational view, partially broken away, of an alternate embodiment of the invention showing in particular, a bracket having an insert slot, a tapered insert in the insert slot, and a tapered arch wire positioned in the insert so as to effect a selected force vector against the tooth.

FIG. 7 of the drawings is a side elevational view, partially broken away, of an alternate embodiment of the orthodontic apparatus of FIG. 1 showing in particular a tooth, a bracket attached to the tooth by means of a band, the bracket having a rectangular insert receiving slot and a rectangular insert installed in the insert receiving slot so as to provide a high slip surface to the slot.

FIG. 8 of the drawings is a side elevational view, partially broken away, of an alternate embodiment of the orthodontic apparatus of FIG. 1 showing in particular a tooth, a bracket having a tapered insert slot and a tapered insert member in the slot.

FIG. 9 of the drawings is a side sectional view of one embodiment of an arch wire for use in the orthodontic apparatus of FIG. 1.

FIG. 10 of the drawings is a side sectional view of an alternative embodiment of an arch wire having a pointed leading edge for use in the orthodontic apparatus of FIG. 1.

FIG. 11 of the drawings is a side sectional view of an alternative embodiment of an arch wire having a tapered leading edge for use in the orthodontic apparatus of FIG. 1.

FIG. 12 of the drawings is a side sectional view of an alternate embodiment of an arch wire having all edges rounded for use in the orthodontic apparatus of FIG. 1.

FIG. 13 of the drawings is a front perspective view, partially broken away, of an arch wire having a series of bends formed therein for use in the orthodontic apparatus of FIG. 1.

FIG. 14 of the drawings is a front perspective view, partially broken away, of a triangular arch wire.

FIG. 15 of the drawings is a bottom elevational view of the arch wire and brackets of FIG. 1 installed on the patient's upper teeth.

DETAILED DESCRIPTION OF THE PREFERRED EMBODIMENT

While the present invention is susceptible of embodiment in many different forms, there is shown in the drawings and will herein after be described in detail several specific embodiments with the understanding that the invention is not limited thereto except insofar as those who have the disclosure before them are able to make modifications and variations therein without departing from the scope of the invention.

As shown in FIG. 1 of the drawings, an orthodontic apparatus 10 for use in altering the position of teeth such as teeth 12 and 14 is shown. A pair of brackets such as brackets 16 and 18 are attached to the front surfaces 20 and 22 of the teeth 12 and 14. In the embodiment shown, the brackets 16 and 18 are attached to the front surfaces 20 and 22 by means of adhesive 24. The brackets 16 and 18 each have a wire receiving slot 26 and 28 formed therein. The wire receiving slot 26 has a pair of non-parallel oppositely disposed slot surfaces 30 and 32. Similarly, the wire receiving slot 28 has a pair of non-parallel slot surfaces 34 and 36. In the embodiment shown, the non-parallel wire surfaces 40 and 42 comprise the occlusal and gingival surfaces of the tapered wire 38. A tapered wire 38 is provided having non-parallel oppositely disposed wire surfaces 40 and 42 formed thereon. The non-parallel oppositely disposed wire surfaces 40 and 42 are configured; i.e., are the correct size and angle for either for slidable positioning of the tapered wire 38 in the wire receiving slots 26 and 28 or selective wedging as required. When the tapered wire 38 is slidable in the wire receiving slots 26 and 28, the position of the tapered wire may be adjusted longitudinally by the orthodontist as required. In the embodiment shown the tapered wire member 38 is formed in a trapezoidal configuration. However, a wide variety of configurations of the tapered wire 38 may be utilized. When the non-parallel wire surfaces 40 and 42 are disposed at an angle of between 25 degrees and 179.5 degrees relative to each other, slidability is provided. The non-parallel slot surfaces 30 and 32 are similarly disposed at an angle of between 25 degrees and 179.5 degrees relative to each other. In order to wedge the arch wire, the angle of taper of the slot surfaces such as surfaces 30 and 32 should be between 1 degree and 25 degrees. In the embodiment shown, the non-parallel wire surfaces 40 and 42 comprise the occlusal and gingival surfaces of the tapered wire 38.

As shown in FIGS. 5 and 14 of the drawings, the tapered wire 38 may be substantially triangular in cross section. Triangular wire generally tends to slide. The non-parallel oppositely disposed wire surfaces 40 and 42 are disposed at substantially the same but not the identical angle relative to each other as the oppositely disposed non-parallel slot surfaces 30 and 32. As indicated above, the brackets 16 and 18 include a mechanism for attaching the brackets to one of the teeth 12 and 14. In the embodiment shown in FIG. 1 the brackets are attached to the teeth by means of adhesive 24. As shown in FIG. 7, a bracket 44 may be attached to the surface 46 of a tooth 48 utilizing a metal band 50 which entirely circumscribes the tooth 48. However, the use of an adhesive compound 24 is preferred.

One of the additional features of the invention, is that the orthodontic apparatus 10 may be self-ligating, i.e, does not require the use of additional ties in order to maintain the position of the tapered wire 38 in the brackets 16 and 18. In order for the tapered wire 38 to be self-ligating, the external configuration of the tapered wire 38 must be substantially identical to the internal configuration of the non-parallel slot surfaces 30 and 32, and between 1 degree and 25 degrees as best shown in FIG. 2. The tapered wire 38 may thereby be wedged into the tapered slot 26, thereby preventing inadvertent pulling of the tapered wire 38 out of the slot 26. An additional feature of the invention is that tapered wire 38 may be selectively removed and replaced with tapered wire having a greater or lesser taper depending on the needs of the patient. For example tapered wire 38 may initially have a taper of between 25 degrees and 179.5 degrees ± one radian so as to facilitate movement of the wire for correction of the position of the brackets such as the brackets 16 and 18. Later in the course of treatment a more fixed positioning of the arch wire 38 may be desired. In such instances, a taper of between 1 degree and 25 degrees ± one radian may be desirable so as to wedge the tapered wire 38 in the wire receiving slot 26.

However, in some instances, use of ligature may be desirable. In those circumstances, as is shown in FIG. 3, a pair of wings 52 and 54 extend from the bracket 56 mounted on a tooth 58. Either a wire or a rubber ligature 60 is wrapped around the wings 52 and 54 with the tapered wire 38 being disposed within the wire receiving slot 62. Again, the bracket 56 has non-parallel slot surfaces 64 and 66 for reception of the tapered wire 38. Both the angle of taper of the slot surfaces 64 and 66 and the size of the wire receiving slot 62 relative to the external configuration of the tapered wire 38 are substantially the same. A difference of as little as 0.5 degrees in taper causes sloppiness of the arch wire in the slot which is undesirable.

As shown in FIG. 2, in the prior art, mounting of a bracket and arch wire on a tooth can cause the tooth to rotate about a center of rotation. Thus the root of the tooth 12a rotates or tips. In many instances, it is desirable for the tooth to remain in substantially the same horizontal plane, but to be moved forwardly or rearwardly. Through the use of selectively applied force vectors such as force vector V, as shown in FIG. 4 the entire tooth may be so moved, so that the root 12b does not tip.

As shown in the FIGS. 1 through 8, the brackets 16, 18, 44 and 56 include a base 68 adapted for attachment to a tooth such as tooth 12. The rear surface 70 of the base best shown in FIG. 2 is substantially flat but slightly curved so as to match the front surface 20 of the tooth 12. As further shown in FIG. 1, a pair of arms 72 and 74 extend substantially normally or perpendicularly from the base 70. The wire receiving slot 26 is disposed therebetween. Alternatively, as shown in FIG. 6, the base 68 may have a rounded crown portion 76 having the wire receiving slot 78 disposed across the surface thereof.

Turning now to FIGS. 9 through 12 of the drawings, a variety of configurations for the arch wire 38 are shown. As shown in FIG. 9, the arch wire may be substantially trapezoidal in cross section. Conversely, the arch wire 38, as shown in FIG. 10, may have tapered non-parallel wire surfaces 40 and 42 and a tapered leading edge 80. The tapered leading edge 80 further facilitates slidable insertion of the arch wire into an orthodontic device such as the brackets 14. As shown in FIG. 11 of the drawings, the tapered leading edge 80 may be rounded. Alternatively, as shown in FIG. 12, not only the tapered leading edge 80 may be rounded but the rear edges 82 and 84 may also be rounded.

As shown in FIGS. 6 and 8 of the drawings, in an additional feature of the invention, an insert such as the insert 86 in FIG. 6 or the insert 88 shown in FIG. 8 is provided. The insert 86 has an external configuration closely conforming to the wire receiving slot 78 in FIG. 6 or the wire receiving slot 92 in FIG. 8. In most instances, it is preferable that the inserts 86 and 88 be fixedly attached to the wire receiving slots 78 and 92 respectively. Alternatively this may be accomplished by having the external configuration of the inserts rectangular and the wire receiving slot similarly shaped so as to wedge therein. Thus, a tab or snap lock 90 may extend (best shown in FIG. 8) from the inserts 86 and 88 which is adapted for mating engagement with a corresponding indentation 91 in the wire receiving slot 78 or 92. A plurality of such tabs 90 and indentations 91 may be provided as desired. It should be noted that in the embodiment in FIGS. 6 and 8, the wire receiving slots 78 and 92 are adapted for receiving the inserts 86 and 88 respectively. Therefore, it is more appropriate to designate the slots as insert receiving slots 78 and 92. The inserts 86 and 88 each have a tapered wire receiving slot 94 and 96 respectively adapted for receiving the tapered wire 38. The angle of taper of the tapered slots 94 and 96 and the angle of the taper of the wire 38 controls and determines the force vector directed against the tooth.

In a preferred embodiment, the insert members 86 and 88 are constructed of a high slip thermoplastic material such as Teflon which facilitates the sliding of the tapered arch wire 38 in the tapered slots 94 and 96.

In the embodiment shown in FIG. 7, the insert receiving slot 97 is substantially rectangular for wedging of the insert 98. Accordingly, the insert 98 attached therein is similarly rectangular in external configuration. Further, in the embodiment shown in FIG. 7, the wire receiving slot 100 of the insert member 98 is substantially rectangular in configuration. Again a high slip thermoplastic material such as Teflon may be utilized to facilitate slidability of the arch wire 38. In this embodiment of the invention, slidability of the arch wire, not selected direction of the force vector are emphasized. Therefore, the arch wire may be rectangular or even rounded. A separate aspect of the invention is thereby shown.

An additional aspect of the invention is the use of a plurality of bracket members such as brackets 102 shown in FIGS. 6 and 8 and a plurality of inserts such as inserts as 86 or 88 for providing a system for progressive orthodontic correction of one or more teeth. The brackets 102 may be of a progressively larger or smaller sizes or formed with their base 68 angled either upwardly, downwardly or to either side. Similarly, the inserts such as insert 86 and 88 are sized for insertion into and retention by the insert receiving slots 78 and 92. Further, the inserts such as inserts 86 and 88 have a selectively tapered wire receiving slot such as slots 94 and 96. These tapered wire receiving slots 94 and 96 are configured so as to supply a selected force vector against the tooth being corrected; i.e, each insert has a selected taper so as to apply a selected force vector. As a result, a series of inserts such as inserts 86 and 88 may be progressively installed and replaced in the wire receiving slots 78 and 92, so as the tooth moves over the course of treatment the force vector applied against the tooth can be changed, as required.

The insert members and/or brackets may be visually coded to indicate the type and degree of correction which the insert member such as inserts 86 and 88 will effect when installed in one of the bracket members such as bracket 102. For example, the inserts may be color coded or contain a number indicating the angle of the tapered slot 94. However, it is evident that the combination of factors involved makes the proper selection of the bracket, insert and slot difficult. Therefore, a chart or microprocessor may be utilized to effect the appropriate selection of elements.

An additional aspect of the invention is the construction of the arch wire 38. The arch wire 38 may have a progressively greater thickness so as to effect increased stiffness of the arch wire in the wire receiving slot 94 thereby increasing the force vector applied to the tooth 12 being corrected. Alternatively, the arch wire 38 may be constructed of a progressively stiffer material so as to effect selectively increased force against the tooth. This increase in stiffness and size may again be evidenced by a visual code again such as a number or a color strip or marking. Although the arch wire may be constructed of a variety of metallic or thermoplastic materials, in a preferred embodiment it is constructed of a nickel titanium alloy so as to provide high strength and flexibility. Alternate materials include "Australian wire" and stainless steel wire.

In order to utilize a plurality of inserts such as inserts 86 and 88, it is desirable to have a tool adapted for inserting and removing the inserts 86 and 88 from the brackets such as bracket 102. Although the tool is not shown, it must contain means for gripping one of the insert members, such as a plier jaws, means for grasping the tool member by the user, such as handles, and an extension between the gripping mechanism and the grasping mechanism such as the arms of a plier.

In the embodiment shown in FIG. 8, the insert 88 extends slightly from the wire receiving slot 92 and therefore can be grasped easily by a tool constructed in the form of tweezers. However, in the embodiment shown in FIGS. 6 and 7, the insert 86 is substantially contained within the wire receiving slot 78. Thus the gripping member in this alternate embodiment of the tool must press simultaneously against the inside surfaces 103 and 103' of the insert member in order to grasp and remove it from the wire receiving slot 78. Alternatively, an indentation on 103" may be formed in the insert member so that the tip of the tool may be inserted into the indentation 103" and the insert pulled from the wire receiving slot 78.

An additional aspect of the present invention is the correction of the position of the tooth 12 in three dimensions simultaneously. In the past utilizing either a rounded or rectangular wire, the teeth were moved either on a horizontal plane or on a directly vertically plane, but with the use of tapered arch wires such as wire 38, a tooth 12 may be moved simultaneously both horizontally and laterally as shown in FIG. 4. This has been previously accomplished in the past utilizing bends in the arch wire, such as shown in FIG. 13. However, the bending of the arch wire to accomplish such correction may be substantially reduced or eliminated utilizing the present system. As is evident from the previous disclosure, in a preferred embodiment the brackets contain a tapered arch wire slot such as wire receiving slot 26 and the arch wire is similarly but not identically tapered. In order to provide the desired degree of correction, a plurality of tapered arch wires and tapered brackets having tapered arch wire slots are provided to the orthodontist. Again the orthodontist observes the position of the patient's teeth and determines the correction required. An arch wire 38 having the desired degree of taper and brackets such as brackets 16 and 18 each having an arch wire slot 26 and 28, exert a specified force vector on the selected teeth of the patient, are selected. The selected brackets such as brackets 16 and 18 are applied to the patient's teeth and the arch wire 38 is applied to the brackets 16 and 18 and the wire receiving slots 26 and 28.

A number of methods are provided for fixing the arch wire in the mouth of a patient. As shown in FIG. 15, in the embodiments described herein the ends of the arch wire 152 and 154 respectively are fixedly attached to oppositely disposed first bracket 156 and oppositely disposed second bracket 158 with the remaining brackets such as bracket 16 and 18 being disposed therebetween. Alternatively buccal tubes, as commonly known in the art may, be utilized. However, a variety of other commonly known devices which are fixedly attached to the teeth and to the ends 152 and 154 of the arch wire may be utilized.

Following attachment of the first end 152 of the arch wire 38 to first bracket 156, the tapered arch wire 38 is inserted through the taper arch wire slots 24 and 26, shown in FIGS. 1 and 2, and placed under desired degree of tension by means of the orthodontist grasping the arch wire 38 with a plier-like tool. The second end 154 of the arch wire 38 is then fixedly attached to the second bracket 158 so as to retain arch wire 38 under tension. As a result, selected correction of the patient's teeth is provided. In addition, the teeth may be moved simultaneously in three dimensions in response to the force vector exerted by the arch wire 38 and the bracket 16.

In an additional embodiment of the invention, a plurality of bracket inserts such as bracket insert 86 shown in FIG. 6 or bracket insert 88 shown in FIG. 8 are provided to the orthodontist. The bracket inserts each have a tapered receiving slot such as tapered slot 94 of FIG. 6. Each of the brackets may have different degrees of taper so as to provide a different force vector against the bracket 76. The brackets may be coded so that the orthodontist can select the appropriate bracket insert. Again, the orthodontist observes the position of the patient's teeth and determines the correction required for the selected teeth. An arch wire is then selected on the basis of the taper of the arch wire. Similarly, a bracket insert such as bracket insert 86 is selected having a desired degree of taper for each tooth to be corrected. As a result a specified force vector is exerted on the patient's teeth in a selected direction. One of the brackets such as bracket 76 is attached to each of the patient's teeth requiring correction. The tapered arch wire 38 is then inserted into the taper arch wire slots. As shown in FIG. 15, the first end 152 of the tapered arch wire 38 is attached to a first bracket 156 on the patient's teeth. The tapered arch wire is placed under a desired degree of tension and the second end 154 of the arch wire 38 is attached to the second bracket 158, first bracket 156 being oppositely disposed from the second bracket 158. The remaining brackets such as bracket 16 and 18 are disposed therebetween, thereby effecting selected correction of the patient's teeth. Thus a novel method of orthodontic correction and system of orthodontic apparati are provided.

What is claimed is:

1. An orthodontic apparatus for use in altering the position of one or more teeth comprising:
   one or more bracket members adapted for mounting upon the surface of a tooth, said bracket members having wire receiving means including a wire receiving slot having oppositely disposed non-parallel slot surfaces; and,
   a tapered wire member having non-parallel oppositely disposed wire surfaces, said oppositely disposed wire surfaces being configured for positioning of said tapered wire member in said wire receiving slot, whereby the position of said tapered wire member may be adjusted in said slot by the orthodontist as required and said tapered wire member is retained therein exclusively by being wedged into the slot.

2. The apparatus of claim 1 wherein said oppositely disposed non-parallel wire surfaces comprise the occlusal and gingival surfaces of said tapered wire member.

3. The apparatus of claim 1 wherein said oppositely disposed wire surfaces are disposed at an angle of between 1 degree and 25 degrees relative to each other so as to facilitate selective wedging between said tapered wire member and said wire receiving slot.

4. The apparatus of claim 1 wherein said bracket member includes means for attaching said bracket to one of said teeth, said means comprising an adhesive compound.

5. The apparatus of claim 1 wherein said bracket member comprises a base adapted for attachment to one of the patient's teeth, and a crown portion having said wire receiving slot disposed across the surface thereof.

6. The apparatus of claim 1 wherein said bracket members each comprise a base member adapted for abutment against the surface of a tooth, the size and angle of said base member relative to said wire receiving means being selected so as to effect a selected force vector against said tooth.

7. An orthodontic apparatus for use in altering the position of one or more teeth comprising:
   one or more bracket members adapted for mounting upon the side of a tooth, said bracket members having wire receiving means including a wire receiving slot having opposite non-parallel slot surfaces disposed at an angle of between about 1 degree and about 25 degrees relative to each other; and,
   a tapered wire member interconnecting said bracket members, said tapered wire member having non-parallel oppositely disposed wire surfaces disposed at substantially the same angle relative to each other as said oppositely disposed non-parallel slot surfaces, said wire receiving slot being sized relative to said wire so as to facilitate selective wedging of said wire in said wire receiving slot and retention therein exclusively by the wedging action.

8. The apparatus of claim 7 wherein said bracket comprises a base adapted for attachment to one of said teeth and a pair of arms disposed substantially normally from said base, said wire receiving slot being disposed between said arms.

9. An orthodontic method utilizing a plurality of tapered arch wires each having progressive greater degrees of taper and a plurality of brackets having tapered arch wire slots, each of said arch wire slots having a progressively greater degree of taper, said method comprising the steps of:

observing the position of the patient's teeth;

determining the correction required for selected teeth of the patient;

selecting an arch wire having a desired degree of taper and a plurality of brackets each having an arch wire slot having a desired degree of taper so as to exert a specified force vector on the selected teeth of the patient in a selected direction;

attaching said selected brackets to the patient's teeth requiring correction in the required positions;

fixedly attaching said arch wire to a first one of said brackets on the patient's teeth;

inserting said tapered arch wire into said tapered arch wire slots in said brackets and retaining said arch wire therein exclusively by wedging said arch wire into said slots;

placing said tapered arch wire under a desired degree of tension; and, fixedly attaching said arch wire to a second one of said brackets on the patient's teeth, said first bracket being oppositely disposed from said second bracket with the remaining brackets on the patient's teeth being disposed therebetween, thereby effecting selected correction of the patient's teeth.

10. The method of claim 9 and further comprising the steps of sliding said tapered arch wire through said tapered arch wire slots so as to connect said brackets.

11. The method of claim 9 and further comprising moving the patient's tooth simultaneously in three dimensions in response to said force vector exerted by said arch wire and said bracket.

12. An apparatus for simultaneous orthodontic correction of one or more teeth in three dimensions comprising:

a plurality of bracket members, each of said bracket members having a tapered wire receiving slot; and, a tapered arch wire having a pair of non-parallel, oppositely disposed surfaces with a taper of between about 1 degree and about 25 degrees relative to one another and secured in said wire receiving slot, said wire connecting said bracket members and having an external configuration substantially identical to the internal configuration of said wire receiving slot to secure said wire within the slot exclusively by wedging action, and said arch wire having a selected degree of stiffness, whereby an arch wire and bracket may be selected so as to effect a predetermined force vector upon said one or more teeth thereby moving said one or more teeth in three dimensions simultaneously.

13. A system for progressive orthodontic correction of one or more teeth comprising:

a plurality of bracket members each of said bracket members including a wire insert receiving slot formed therein;

means for attaching said bracket member to said teeth;

a plurality of tapered arch wires for connecting said bracket members together exclusively by wedging said wires into the receiving slot of the bracket members; and, each of said arch wires and said brackets being configured so as to apply a selected force vector against said teeth so that a series of said arch wires may be progressively installed and replaced in said bracket members over a period of time so as to selectively alter said force vectors applied against said teeth.

* * * * *